(12) United States Patent
Ostermeier et al.

(10) Patent No.: US 8,993,753 B2
(45) Date of Patent: Mar. 31, 2015

(54) STEREOSELECTIVE SYNTHESIS OF BICYCLIC HETEROCYCLES

(71) Applicants: Markus Ostermeier, Biberach an der Riss (DE); Juergen Daeubler, Ummendorf (DE); Guenther Huchler, Hochdorf (DE); Stephan Kling, Warthausen (DE); Marco Santagostino, Mittelbiberach (DE)

(72) Inventors: Markus Ostermeier, Biberach an der Riss (DE); Juergen Daeubler, Ummendorf (DE); Guenther Huchler, Hochdorf (DE); Stephan Kling, Warthausen (DE); Marco Santagostino, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/154,441

(22) Filed: Jan. 14, 2014

(65) Prior Publication Data

US 2014/0135495 A1    May 15, 2014

Related U.S. Application Data

(62) Division of application No. 12/846,943, filed on Jul. 30, 2010, now Pat. No. 8,658,790.

(30) Foreign Application Priority Data

Aug. 6, 2009   (EP) .................................... 09167393

(51) Int. Cl.
| | | |
|---|---|---|
| *C07D 239/72* | (2006.01) | |
| *C07D 403/12* | (2006.01) | |
| *C07D 239/70* | (2006.01) | |
| *C07D 241/38* | (2006.01) | |

(52) U.S. Cl.
CPC ............ *C07D 403/12* (2013.01); *C07D 239/70* (2013.01); *C07D 241/38* (2013.01)
USPC ......................................... 544/231; 544/224

(58) Field of Classification Search
CPC ...................................................... C07D 239/72
USPC .................................. 544/224, 231
See application file for complete search history.

(56) References Cited

U.S. PATENT DOCUMENTS

| | | | |
|---|---|---|---|
| 7,998,949 B2 | 8/2011 | Himmelsbach et al. | |
| 8,263,768 B2 * | 9/2012 | Ostermeier et al. | ........... 544/283 |
| 8,497,369 B2 * | 7/2013 | Himmelsbach et al. | ....... 544/253 |
| 8,629,146 B2 * | 1/2014 | Schnaubelt et al. | ........ 514/252.1 |
| 8,658,790 B2 * | 2/2014 | Ostermeier et al. | ........... 544/231 |
| 8,853,225 B2 * | 10/2014 | Pfrengle et al. | ............. 514/266.2 |
| 2009/0170908 A1 | 7/2009 | Shimada et al. | |
| 2011/0046148 A1 | 2/2011 | Himmelsbach et al. | |
| 2013/0030003 A1 | 1/2013 | Pfrengle et al. | |

FOREIGN PATENT DOCUMENTS

| | | |
|---|---|---|
| WO | 03082831 A1 | 10/2003 |
| WO | 2009098061 A1 | 8/2009 |
| WO | 2012104206 A1 | 8/2012 |

OTHER PUBLICATIONS

International Search Report for PCT/EP2010/061096 mailed Nov. 16, 2010.
U.S. Appl. No. 13/761,211, filed Feb. 7, 2013.

\* cited by examiner

*Primary Examiner* — Golam M M Shameem
(74) *Attorney, Agent, or Firm* — Michael P. Morris; Edward S. Lazer

(57) ABSTRACT

The present invention relates to a process for the stereoselective preparation of compounds of formulae (1A) and (1B)

(1A)

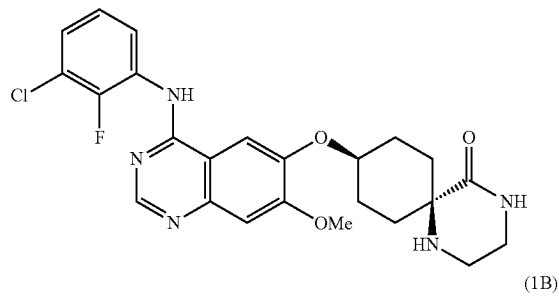

(1B)

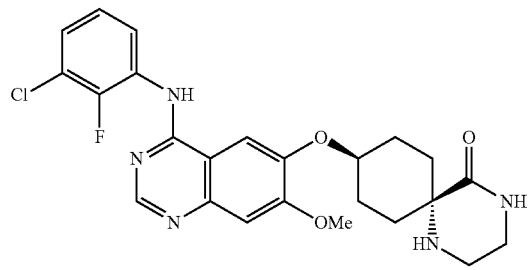

and the salts thereof, particularly the physiologically acceptable salts thereof with inorganic or organic acids and bases, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways.

1 Claim, No Drawings

STEREOSELECTIVE SYNTHESIS OF BICYCLIC HETEROCYCLES

This application is a divisional of U.S. Ser. No. 12/846,943 filed Jul. 30, 2010, which claims priority to European Patent Application No. 09167393.9, filed Aug. 6, 2009, which are hereby incorporated herein by reference in their entireties.

The present invention relates to processes for the stereoselective preparation of compounds of formulae (1A) and (1B)

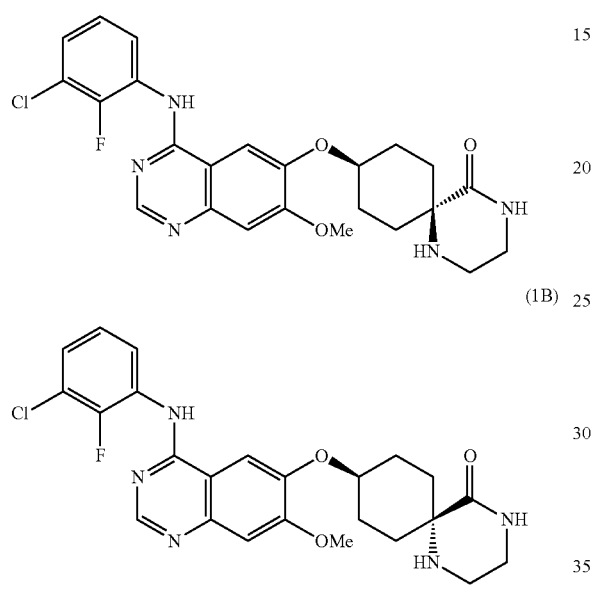

and the salts thereof, particularly the physiologically acceptable salts thereof with inorganic or organic acids and bases, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways.

BACKGROUND TO THE INVENTION

Quinazoline derivatives are known from the prior art as active substances, for example, for the treatment of tumoral diseases as well as diseases of the lungs and airways. Processes for preparing quinazoline derivatives are described in WO03082831.

The problem of the present invention is to provide a stereoselective process for preparing the quinazoline derivatives according to the invention.

DESCRIPTION OF THE INVENTION

The present invention solves the above-mentioned problem by means of the method of synthesis described hereinafter.

The invention thus relates to a process for the stereoselective preparation of the compound of formula (1A)

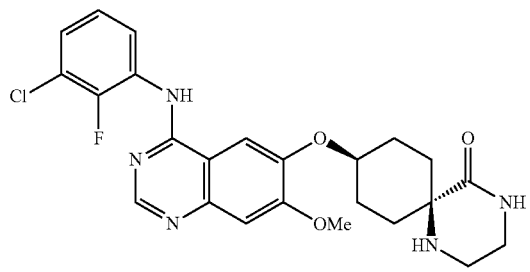

optionally in the form of the tautomers thereof, and optionally the pharmacologically acceptable acid addition salts thereof, characterised in that the process comprises reaction steps (A), (B), (V), (X), (R), (S) and (T), wherein (A) denotes the reaction of 1,4-cyclohexanedione-monoethyleneketal to form a compound of formula (1)

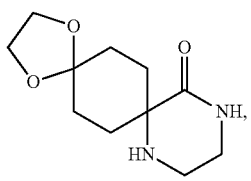

(B) denotes the reaction of a compound of formula (1) to form the compound of formula (2)

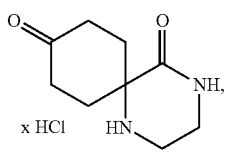

(V) denotes the reaction of a compound of formula (2) with a protective group reagent, preferably with benzyl chloroformate, to form the compound of formula (19)

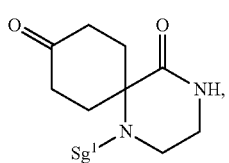

(X) denotes the reaction of a compound of formula (19) to form the compound of formula (18)

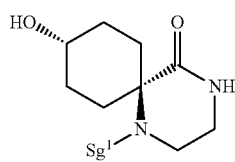

(R) denotes the reaction of a compound of formula (18) with a compound of formula (23)

to form a compound of formula (21)

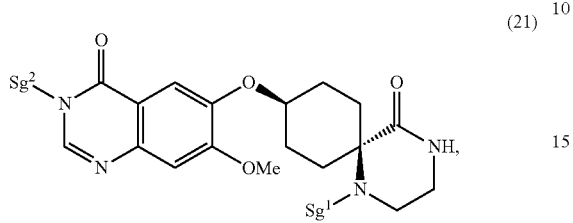
(21)

(S) denotes the cleavage of the protective groups, preferably of the benzyl group and of the Cbz group, of the compound of formula (21) to form a compound of formula (22)

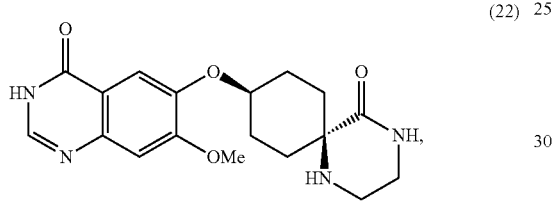
(22)

and (T) denotes the chlorination of the compound of formula (22) and subsequent reaction with 3-chloro-2-fluoroaniline, while steps (A) to (T) take place successively in the order stated and the protective group $Sg^1$ may represent a group selected from among optionally substituted benzyl, Cbz and optionally substituted acetyl, preferably trifluoroacetyl, particularly preferably Cbz, and the protective group $Sg^2$ may represent optionally substituted benzyl, preferably benzyl.

Also preferred is a process for the stereoselective preparation of compounds of formula (1A), characterised in that the process consists of process steps (R), (S) and (T).

Also preferred is a process for the stereoselective preparation of a compound of formula (18), characterised in that the process consists of process steps (A), (B), (V) and (X).

The invention further relates to a process for the stereoselective preparation of the compound of formula (1B)

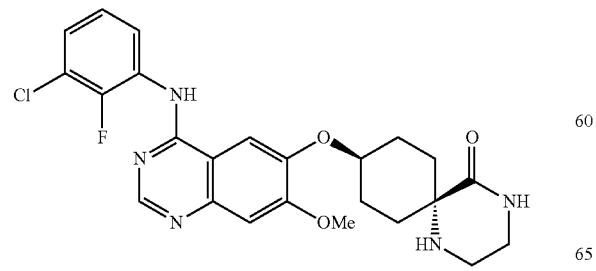
(1B)

optionally in the form of the tautomers thereof, and optionally the pharmacologically acceptable acid addition salts thereof, characterised in that the process includes the reaction steps (A), (B), (Z), (H), (P), (Q), (M), (N) and (O), wherein (A) denotes the reaction of 1,4-cyclohexanedione-mono-ethyleneketal to form a compound of formula (1)

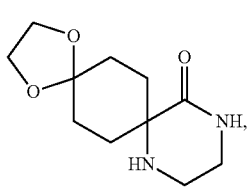
(1)

(B) denotes the reaction of a compound of formula (1) to form the compound of formula (2)

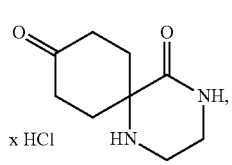
(2)

(Z) denotes the reaction of a compound of formula (2) to form the compound of formula (16)

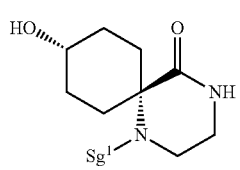
(16)

(H) denotes the reaction of a compound of formula (16) to form the compound of formula (6)

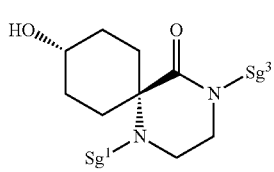
(6)

(P) denotes the reaction of a compound of formula (6) with a compound of formula (23)

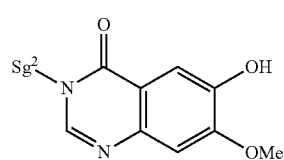
(23)

to form a compound of formula (7)

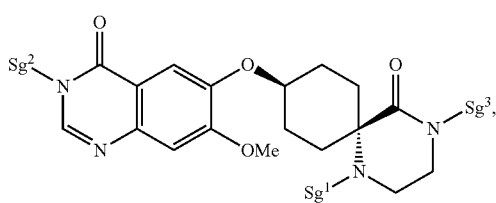
(7)

(Q+M) denotes the cleavage of the protective groups from the compound of formula (7) to form a compound of formula (12)

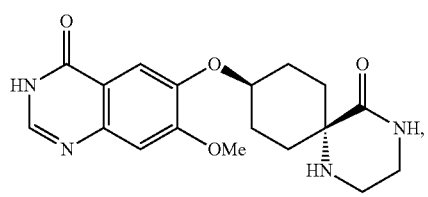
(12)

and (N+O) denotes the chlorination of the compound of formula (12) and subsequent reaction with 3-chloro-2-fluoroaniline, while steps (A) to (O) take place successively in the order stated and the protective group $Sg^1$ may represent a group selected from among optionally substituted benzyl, Cbz and optionally substituted acetyl, preferably trifluoroacetyl, particularly preferably Cbz, the protective group $Sg^2$ may represent optionally substituted benzyl, preferably benzyl.

The invention further relates to a process for the stereoselective preparation of a compound of formula (1B), characterised in that in the process the process steps [(Z), (H)] are replaced by the process steps [(C), (D), (E) or (F), and (G)], wherein (C) represents the reaction of a compound of formula (2) to form the compound of formula (3)

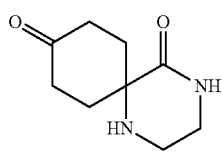
(3)

(D) represents the reaction of a compound of formula (3) to form the compound of formula (4)

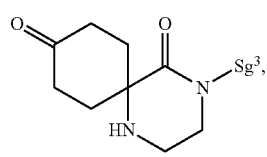
(4)

(E) or (F) represents the reaction of a compound of formula (4) to form the compound of formula (5)

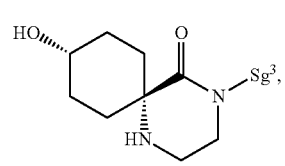
(5)

while in step (F) compound (5) is not isolated, and (G) represents the reaction of a compound of formula (5) to form the compound of formula (6)

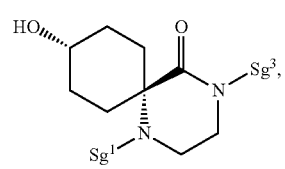
(6)

while steps (C) to (G) take place successively in the order stated and the protective group $Sg^1$ may represent a group selected from among optionally substituted benzyl, Cbz and optionally substituted acetyl, preferably trifluoroacetyl, particularly preferably Cbz, the protective group $Sg^3$ may represent a group selected from among Boc and allyloxycarbonyl, particularly preferably Boc.

The invention further relates to a process for the stereoselective preparation of a compound of formula (1B), characterised in that in the process the process steps [(P), (Q), (M)] are replaced by the process steps [(I), (J), (K), (L)], wherein (I) denotes the reaction of a compound of formula (6) with a compound of formula (15)

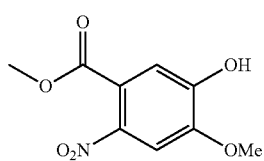
(15)

to form the compound of formula (9)

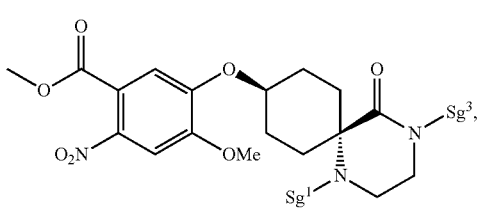
(9)

(J+K) denotes the cleavage of the protective groups and hydrogenolytic reduction of a compound of formula (9) to form the compound of formula (11)

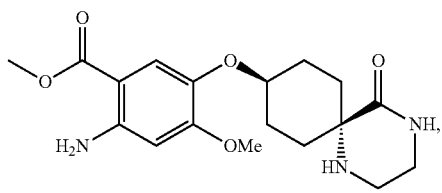

(11)

and
(L) denotes the reaction of a compound of formula (11) to form the compound of formula (12)

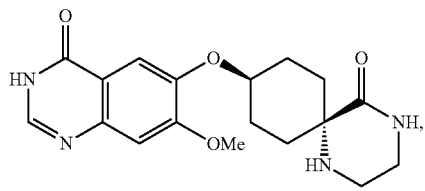

(12)

while steps (I) to (L) take place successively in the order stated and the protective group $Sg^1$ may represent a group selected from among optionally substituted benzyl, Cbz and optionally substituted acetyl, preferably trifluoroacetyl, particularly preferably Cbz, the protective group $Sg^3$ may represent a group selected from among Boc and allyloxycarbonyl, particularly preferably Boc.

The invention further relates to the compound of formula 1A, as well as the pharmacologically acceptable salts, hydrates, solvates and co-crystals thereof.

The invention further relates to the compound of formula 1B, as well as the pharmacologically acceptable salts, hydrates, solvates and co-crystals thereof.

The invention further relates to the compound of formula 18, as well as the pharmacologically acceptable hydrates, solvates and co-crystals thereof.

The invention further relates to the compound of formula 22, as well as the pharmacologically acceptable salts, hydrates, solvates and co-crystals thereof.

The invention further relates to the compound of formula 13, as well as the pharmacologically acceptable salts, hydrates, solvates and co-crystals thereof.

The invention further relates to the compound of formula 4, as well as the pharmacologically acceptable salts, hydrates, solvates and co-crystals thereof.

The invention further relates to the compound of formula 5, as well as the pharmacologically acceptable salts, hydrates, solvates and co-crystals thereof.

The invention further relates to the compound of formula 6, as well as the pharmacologically acceptable hydrates, solvates and co-crystals thereof.

The invention further relates to the compound of formula 12, as well as the pharmacologically acceptable salts, hydrates, solvates and co-crystals thereof.

By co-crystals are meant, within the scope of the present invention, molecular complexes which contain two or more different molecules in the same crystal lattice (Crystal Growth & Design, 2009, Vol. 9, No. 6, 2950-2967; Stahly, G. P. Cryst. Growth Des. 2007, 7, 1007-1026), particularly co-crystals that are formed between a molecular or ionic pharmaceutical active substance molecule and a co-crystal forming agent that is present as a solid at ambient temperature (Jones, W.; Motherwell, W. D.; Trask, A. V. MRS Bull. 2006, 341, 875-879; Vishweshwar, P.; McMahon, J. A.; bis, J. A.; Zaworotko, M. J., J. Pharm. Sci. 2006, 95, 499-516).

Also particularly preferred is a process in which a chlorinating agent selected from among thionyl chloride, phosphorus oxychloride, an N-chlorosuccinimide/triphenylphosphane combination and a carbon tetrachloride/triphenylphosphane combination is used.

The compounds according to the invention may be present in the form of the tautomers as well as in the form of the free bases or the corresponding acid addition salts with pharmacologically acceptable acids—such as for example acid addition salts with hydrohalic acids, for example hydrochloric or hydrobromic acid, inorganic acids, for example phosphoric acid or sulphuric acid or organic acids, such as for example oxalic, fumaric, diglycolic, toluenesulphonic, benzoic, succinic, maleic, salicylic, malic or methanesulphonic acid.

In the process steps described above, it is preferable to use the following solvents selected from the group mentioned in each case:
In process step
A: $CH_2Cl_2$, $CHCl_3$, THF (tetrahydrofuran) and dioxane
B: HOAc, $H_2O$, aqueous solutions of the following solvents: EtOH, THF, iPrOH, MeOH, NMP (N-methyl-2-pyrrolidone) and DMF (dimethylformamide)
V: THF, dioxane, NMP, Me-THF and ACN (acetonitrile)
X: THF/EtOH/$H_2O$ and dioxane/MeOH/$H_2O$
R: NMP, dioxane, DMF, THF and $CH_2Cl_2$
S: EtOH/$H_2O$/HCl, HOAc and MeOH/$H_2O$/HCl
T: ACN and NMP
Z: aqueous NaOH and aqueous KOH, and additionally EtOH, MeOH, THF
P: NMP, dioxane, THF and $CH_2Cl_2$
Q: dioxane, THF, NMP, $CH_2Cl_2$ and EtOH
M: HOAc/$H_2O$, HCl/EtOH and HCl/MeOH
N: dioxane/ACN and THF/ACN
O: HCl/$H_2O$, NMP, dioxane and THF
C: ACN, EtOH, MeOH, iPrOH, $H_2O$, THF and NMP
D: ACN, THF and NMP
E: $H_2O$, EtOH, THF and dioxane
F: $H_2O$, THF, dioxane and EtOH
G: $H_2O$/THF, THF, NMP, $CH_2Cl_2$ and dioxane
I: NMP, THF, dioxane, $CH_2Cl_2$, toluene and DMF
J: dioxane, THF, NMP, $CH_2Cl_2$ and EtOH
K: EtOH, MeOH, iPrOH, NMP, dioxane and THF
L: nPrOH, EtOH, MeOH, NMP and ACN The process steps described above are preferably carried out in the following temperature ranges:
In process step:
A: preferably −15 to 40° C., particularly preferably −10 to 10° C.,
B: preferably 20 to 75° C., particularly preferably 35 to 55° C.,
V: preferably 0 to 50° C., particularly preferably 10 to 35° C.,
X: preferably 0 to 60° C., particularly preferably 5 to 35° C.,
R: preferably 5 to 100° C., particularly preferably 15 to 40° C.,
S: preferably 50 to 80° C., particularly preferably 65 to 80° C.,
T: preferably 10 to 80° C., particularly preferably 15 to 50° C.,
Z: preferably 0 to 60° C., particularly preferably 10 to 35° C.,
H: preferably 15 to 60° C., particularly preferably 15 to 30° C.,
P: preferably 10 to 80° C., particularly preferably 15 to 35° C.,
Q: preferably 0 to 80° C., particularly preferably 50 to 70° C.,
M: preferably 20 to 90° C., particularly preferably 60 to 80° C., N: preferably 15 to 85° C., particularly preferably 70 to 85° C.,
O: preferably 0 to 80° C., particularly preferably 10 to 50° C.,
C: preferably 0 to 65° C., particularly preferably 15 to 30° C.,
D: preferably 10 to 80° C., particularly preferably 20 to 40° C.,
E: preferably 0 to 40° C., particularly preferably 0 to 15° C.,
F: preferably 0 to 45° C., particularly preferably 10 to 25° C.,
G: preferably 0 to 45° C., particularly preferably 10 to 25° C.,
I: preferably 0 to 50° C., particularly preferably 15 to 30° C.,
J: preferably 0 to 85° C., particularly preferably 40 to 70° C.,
K: preferably 10 to 60° C., particularly preferably 15 to 35° C., and
L: preferably 60 to 97° C., particularly preferably 85 to 97° C., In process steps K, M and S, catalysts selected from among Pd/C, Pd(OH)$_2$ preferably Pd/C, are preferably used.

Protective groups selected from among benzyl, Cbz, trifluoroacetyl and Boc are preferably used.

The abbreviation Boc used in the above formulae denotes tertiary butyl carbamate and Cbz denotes benzyloxycarbonyl.

By the term "optionally substituted benzyl" are meant for example groups selected from among benzyl, para-methoxybenzyl, para-methylbenzyl and 1-phenylethyl, particularly preferably benzyl.

By the term "optionally substituted acetyl" are meant for example groups selected from among trifluoroacetyl, acetyl, monofluoroacetyl, difluoroacetyl and trichloroacetyl, particularly preferably trifluoroacetyl.

Schemes 1 and 2 illustrate the synthesis according to the invention. All the compounds are shown in the form of their bases.

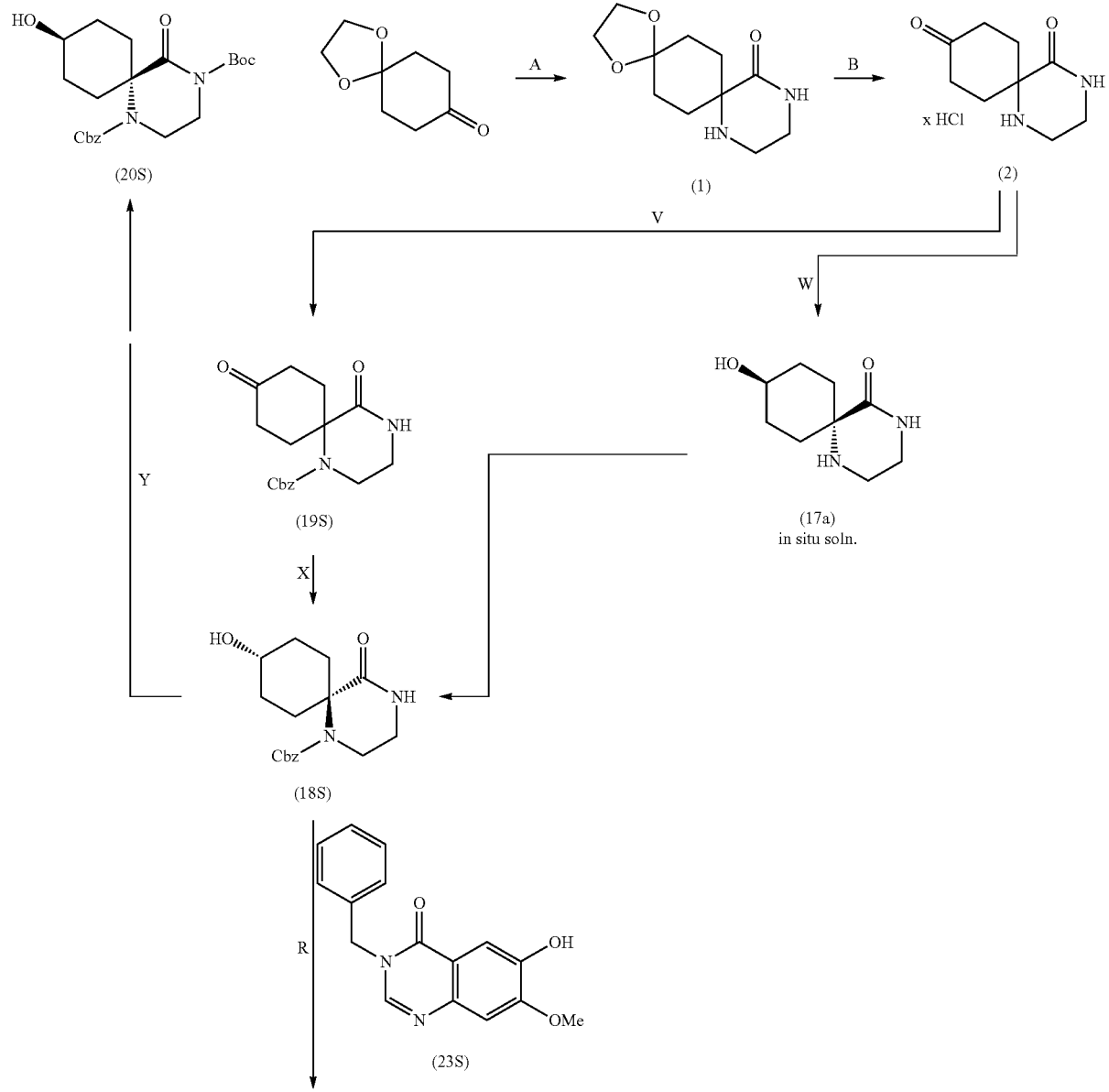

Scheme 1 Synthesis steps for preparing compound (1A)

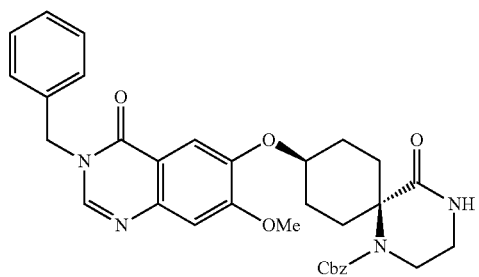
(21S)
S ↓
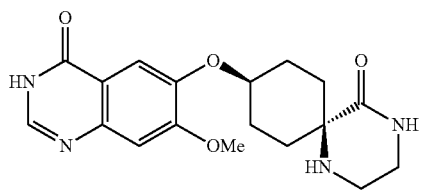
(22)
T ↓
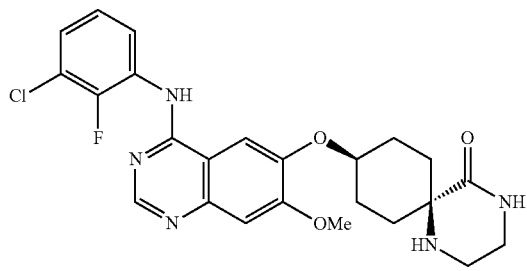
(1A)
Scheme 2 Synthesis steps for preparing compound (1B)
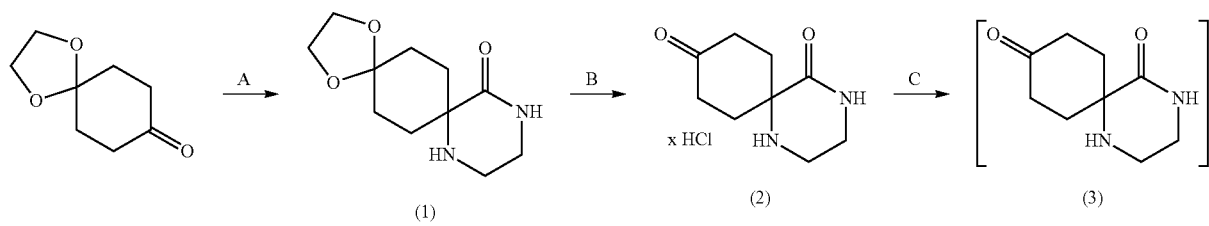

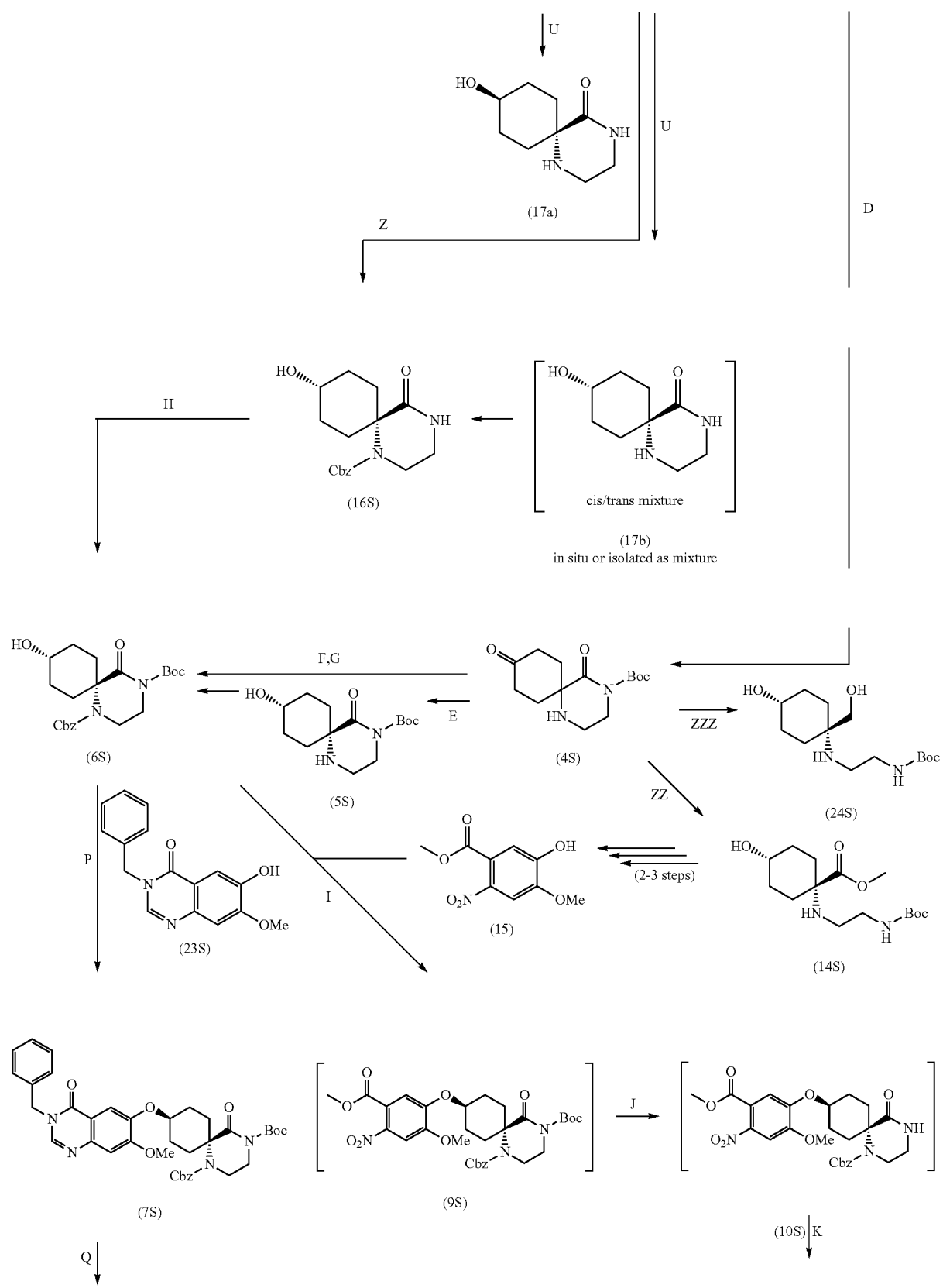

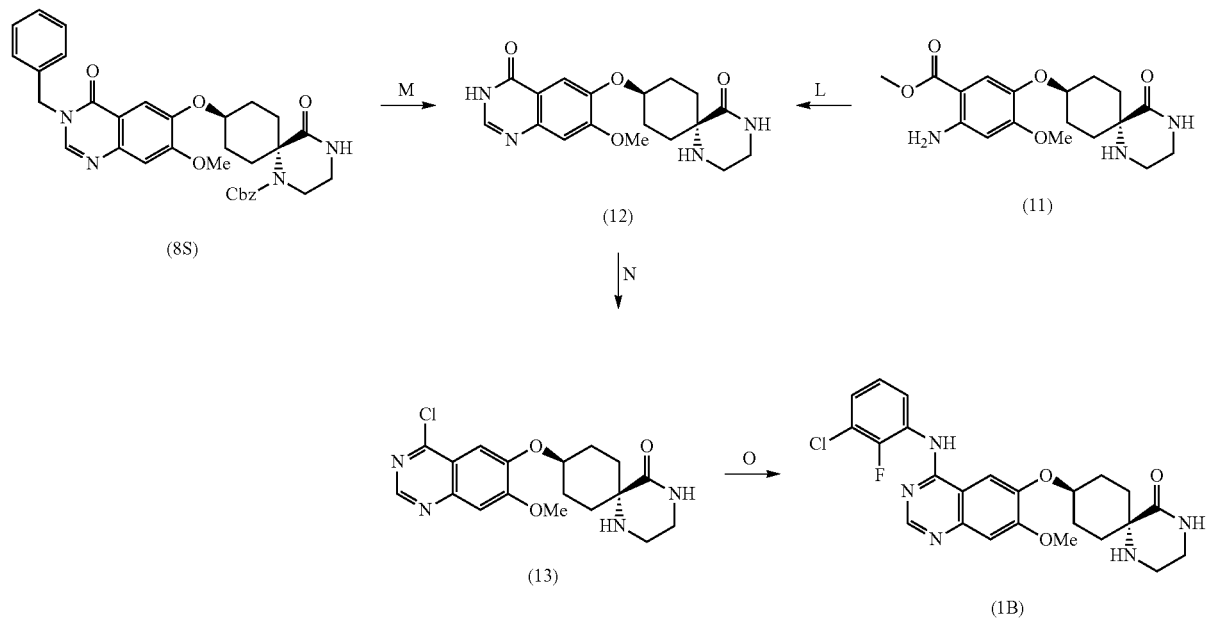

The following Examples serve to illustrate the processes carried out by way of example for preparing the compounds of formulae (1A) and (1B). These Examples are intended as an illustration of the invention without restricting it to the subject-matter thereof.

Example 1

1,4-dioxa-9,12-diaza-dispiro[4.2.5.2]pentadecan-13-one

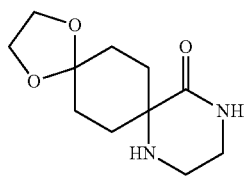

(1)

Process Step A 127.5 ml of ethylenediamine in 194 ml chloroform are added dropwise to a mixture of 250 g of 1,4-cyclohexanedione-mono-ethyleneketal, 18.2 g benzyltriethylammonium chloride and 1.57 g of sodium cyanide in 1 l dichloromethane which has been cooled to −5° C. Then at approx. −10 to 0° C., 407.5 ml of 50% sodium hydroxide solution are added dropwise within the next 9 h. After 14.5 h at −5 to 25° C., 500 ml conc. hydrochloric acid are added dropwise. The precipitate is filtered off and washed twice with 500 ml dichloromethane. The filtrate is phase-separated. The aqueous phase is extracted twice with 1 l dichloromethane and once with 500 ml dichloromethane. The combined organic phases are dried on sodium sulphate and evaporated down in vacuo. 500 ml of n-butyl acetate are added and evaporation is continued until 820 g suspension remain. At 50° C., 3 l methyl-tert-butylether are added within 20 min. The precipitate is suction filtered and washed twice with 200 ml of methyl-tert-butylether. After drying 247 g of product is obtained.

Mass spectrum (ESI+): m/z=227 [M+H]+

Example 2

1,4-diaza-spiro[5.5]undecane-5,9-dione

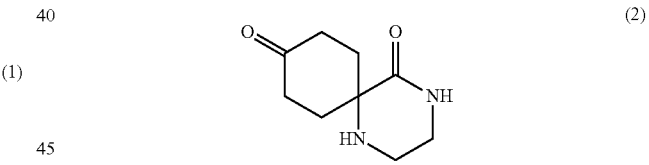

Process Step B 310 ml of 10M HCl in ethanol are added dropwise to 500 g of 1,4-dioxa-9,12-diaza-dispiro[4.2.5.2]pentadecan-13-one in 2.5 l acetic acid within 45 min. After 3 h at 35-45° C., 10 l of isopropanol are added dropwise within 20 min. The suspension is cooled to 15° C. and filtered. The precipitate is washed twice with 1 l of isopropanol and twice with 1 l of methyl-tert-butylether. After the solid is dried 386 g of product is obtained as the hydrochloride.

Mass spectrum (ESI+): m/z=183 [M+H]+

Process Step C 380 g 1,4-diaza-spiro[5.5]undecane-5,9-dione hydrochloride in 3.8 l acetonitrile are combined with 320 ml of 30% sodium methoxide solution in methanol within one hour. 18 g sodium carbonate are added and the mixture is stirred for 18 h. 2 l of solvent are distilled off and the residue is filtered. The filter cake is washed twice with 100 ml acetonitrile and the filtrate which contains the product is further reacted directly in the next step.

Example 3 tert-butyl 5,9-dioxo-1,4-diaza-spiro[5.5]undecane-4-carboxylate

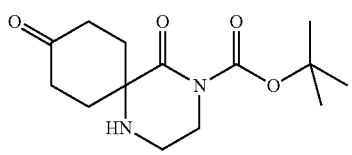
(4S)

Process Step D 480 g potassium carbonate and 10 g 4-(dimethylamino)-pyridine are added to the solution of the previous mixture, which contains the 1,4-diaza-spiro[5.5]undecane-5,9-dione. 415 g of di-tert-butyldicarbonate in 415 ml acetonitrile are added dropwise within 200 min. After 18.5 h 10 g 4-(dimethylamino)-pyridine and 100 g di-tert-butyldicarbonate in 100 ml acetonitrile are added. After 200 min, 100 g di-tert-butyldicarbonate in 100 ml acetonitrile are added. After 90 min 50 g di-tert-butyldicarbonate in 50 ml acetonitrile are added. After 1 h, 2 l water are added. After phase separation the aqueous phase is washed with 1 l methyl-tert-butylether. The combined organic phases are washed with 1 l of 10% potassium carbonate solution and 500 ml of sat. saline solution. The organic phase is evaporated down in vacuo. 1.5 l of n-butyl acetate are added to the suspension and it is evaporated down again. Another 2 l of n-butyl acetate are added and the mixture is evaporated down again. The suspension remaining is heated to 55° C. and slowly combined with 1 l methyl-tert-butylether. The suspension is cooled to 22° C. The precipitate is filtered off and washed with 500 ml n-butyl acetate and 500 ml methyl-tert-butylether. After the solid is dried, 296 g of the product are obtained.

Mass spectrum (ESI$^+$): m/z=283 [M+H]$^+$

Example 4 tert-butyl(cis)-9-hydroxy-5-oxo-1,4-diaza-spiro[5.5]undecane-4-carboxylate

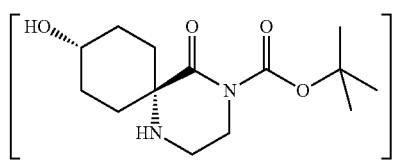
(5S)

Process Step E 6.4 g sodium borohydride in 100 ml of water are added dropwise within 17 min, at 1° C., to a mixture of 159 g tert-butyl 5,9-dioxo-1,4-diaza-spiro[5.5]undecane-4-carboxylate in 1140 ml of water. The dropping funnel is rinsed with 30 ml of water. After 50 min, 318 ml of sat. potassium carbonate solution are added and after stirring for 1 h at 10° C. the precipitate is suction filtered and washed twice with 200 ml 10% potassium carbonate solution. After drying the precipitate is stirred in 1.6 l water for 4.5 h. 350 ml of sat. potassium carbonate solution are added and after stirring for 15 min the precipitate is suction filtered and washed with 200 ml of 10% potassium carbonate solution. After drying the precipitate is stirred in 500 ml of tetrahydrofuran for 20 min. After filtration, washing with 200 ml of tetrahydrofuran and evaporation of the filtrate, 65.5 g product is obtained.

Mass spectrum (ESI$^+$): m/z=285 [M+H]$^+$

Process Step F 3.8 g sodium borohydride in 30 ml of water are added dropwise to a solution of 113 g of tert-butyl 5,9-dioxo-1,4-diaza-spiro[5.5]undecane-4-carboxylate in 1150 ml THF and 25 ml of water at 16° C. within 20 min. After 45 min, 0.42 g sodium borohydride are added. After 35 min 0.42 g of sodium borohydride are added. After another 35 min, 0.1 g sodium borohydride are added. After 15 min, 10 ml acetone are added and the reaction mixture is washed twice with 500 ml of sat. saline solution. The organic phase is used directly in the next experiment.

Mass spectrum (ESI$^+$): m/z=285 [M+H]$^+$

Example 5

1-benzyl 4-tert-butyl(cis)-9-hydroxy-5-oxo-1,4-diaza-spiro[5.5]undecane-1,4-dicarboxylate

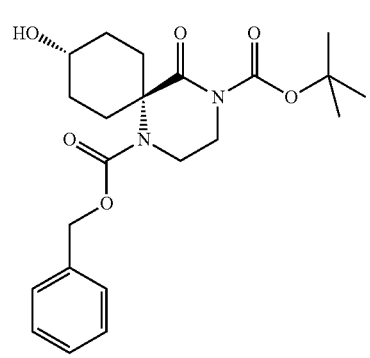
(6S)

Process Step G 112 ml of sat. potassium carbonate solution are added to the organic phase from the previous mixture and then 59 ml benzyl chloroformate are added dropwise within 20 min. After 16 h 400 ml of water are added and the phases are separated. The organic phase is washed with 900 ml sat. potassium carbonate solution and twice with 450 ml sat. saline solution. The organic phase is dried on magnesium sulphate and then evaporated down. After 1 l has been distilled off, 450 ml methylcyclohexane are added and the mixture is evaporated further. Another 100 ml methylcyclohexane are added twice more and the mixture is evaporated down further until 168 crude product remain. The crude product is recrystallised three times from methanol/water 1:1. After drying 86 g product are obtained.

Mass spectrum (ESI$^+$): m/z=419 [M+H]$^+$

Process Step H

A mixture of 500 mg benzyl(cis)-9-hydroxy-5-oxo-1,4-diaza-spiro[5.5]undecane-1-carboxylate, 217 mg potassium carbonate, 686 mg di-tert-butyldicarbonate and 192 mg 4-(dimethylamino)-pyridine in 10 ml acetonitrile are stirred for 4 h at RT. The mixture is purified by two runs of chromatography on silica gel and 420 mg of product are obtained.

Mass spectrum (ESI$^+$): m/z=419 [M+H]$^+$

Example 6

Methyl 5-hydroxy-4-methoxy-2-nitro-benzoate

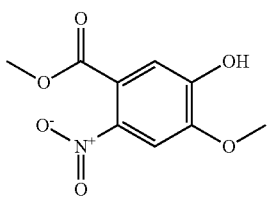
(15)

A mixture of 500 g methyl 4,5-dimethoxy-2-nitro-benzoate and 625 g potassium hydroxide in 2300 ml of water is heated to 95° C. for 18.5 h. After cooling, the mixture is filtered clear and the filtrate is diluted with 3 l water. The solution is combined with 950 ml acetic acid and after 1 h the precipitate is filtered off. The precipitate is suspended in 3250 ml ethyl acetate and then 100 ml of water and 200 ml 12N hydrochloric acid are added. After 1.5 h the phases are separated and the aqueous phase is extracted with 700 ml ethyl acetate. The combined organic phases are dried on magnesium sulphate and after filtration they are evaporated down. The mixture is evaporated again with 200 ml methylcyclohexane. The residue is refluxed together with 1600 ml of methanol and 100 ml conc. sulphuric acid for 16.5 h. The mixture is evaporated down until crystallisation begins. 1000 ml of water are added and the mixture is stirred until a homogeneous suspension is obtained. The precipitate is filtered off, washed with 500 ml of water and suspended in 1000 ml of water. After 1.5 h stirring the precipitate is filtered off and washed with 500 ml of water. After the filter cake is dried, 364 g product are obtained.

Mass spectrum (ESI$^-$): m/z=226 [M−H]$^+$

Example 7

1-benzyl 4-tert-butyl(trans)-9-(2-methoxy-5-methoxycarbonyl-4-nitro-phenoxy)-5-oxo-1,4-diaza-spiro[5.5]undecane-1,4-dicarboxylate

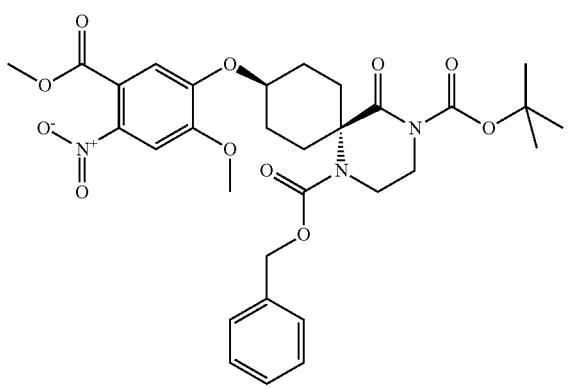
(9S)

Process Step I 58.75 ml diisopropylazo-dicarboxylate are added dropwise at RT within one hour to a mixture of 99 g 1-benzyl 4-tert-butyl(cis)-9-hydroxy-5-oxo-1,4-diaza-spiro[5.5]undecane-1,4-dicarboxylate, 53.74 g methyl 5-hydroxy-4-methoxy-2-nitro-benzoate (15) and 74.34 g triphenylphosphine in 764 ml dioxane. After 17 h, 5 ml of diisopropyl azo-dicarboxylate are added and the mixture is stirred for a further 1.5 h. The mixture which contains the product is further reacted directly in the next step without purification.

Mass spectrum (ESI$^+$): m/z=645 [M+NH4]$^+$

Example 8

Benzyl(trans)-9-(2-methoxy-5-methoxycarbonyl-4-nitro-phenoxy)-5-oxo-1,4-diazaspiro[5.5]undecane-1-carboxylate

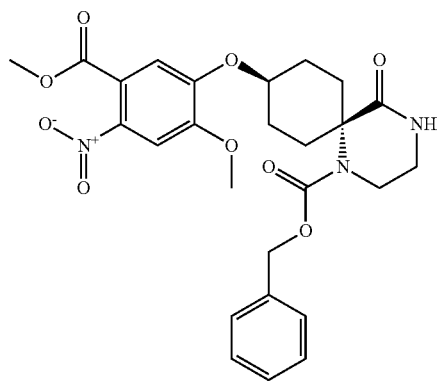
(10S)

Process Step J 130 ml of 4M HCl in dioxane are added to the previous mixture which contains the 1-benzyl 4-tert-butyl(trans)-9-(2-methoxy-5-methoxycarbonyl-4-nitro-phenoxy)-5-oxo-1,4-diaza-spiro[5.5]undecane-1,4-dicarboxylate. The reaction mixture is heated to 60° C. After 2 h a further 13 ml of 4M HCl in dioxane are added. The reaction solution is cooled to RT and combined with 500 ml of sat. potassium carbonate solution. The organic phase is washed with 500 ml of sat. potassium carbonate and 200 ml of sat. saline solution. The organic phase which contains the product is further reacted directly in the next step without purification.

Mass spectrum (ESI$^+$): m/z=528 [M+H]$^+$

Example 9

Methyl(trans)-2-amino-4-methoxy-5-(5-oxo-1,4-diaza-spiro[5.5]undec-9-yloxy)-benzoate

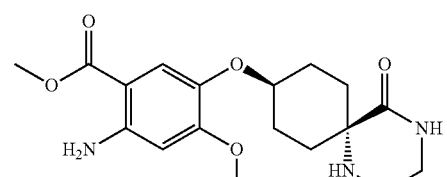
(11)

Process Step K 12.4 g of Pd (10%) on charcoal and 500 ml of methanol are added to the previous mixture, which contains the benzyl (trans)-9-(2-methoxy-5-methoxycarbonyl-4-nitro-phenoxy)-5-oxo-1,4-diazaspiro[5.5]undecane-1-carboxylate. After hydrogenation with hydrogen for 1.5 h at 3 bar the mixture is evaporated down to a residual volume of 600 ml. The mixture is diluted with 1.8 l dioxane and filtered clear. 59 ml of 4M HCl in dioxane are added dropwise within 45 min and after another 30 min the precipitate is suction filtered and washed twice with 200 ml dioxane. After the solid has been dried 98.6 g of the product are obtained as the hydrochloride.

Mass spectrum (ESI⁺): m/z=364 [M+H]⁺

Example 10

(trans)-9-(4-hydroxy-7-methoxy-quinazolin-6-yloxy)-1,4-diaza-spiro[5.5]undecan-5-one

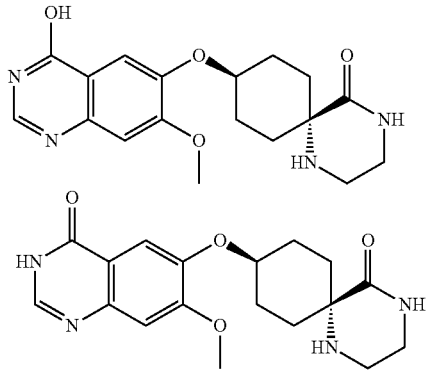

(12)

Process Step L 88 g methyl(trans)-2-amino-4-methoxy-5-(5-oxo-1,4-diaza-spiro[5.5]undec-9-yloxy)-benzoate hydrochloride and 25 g formamidine acetate in 1.8 L of n-propanol are refluxed for 17 h. Then the mixture is cooled to 28° C. and stirred for 4 h at this temperature. After cooling to 14° C. the precipitate is filtered off and washed with 200 ml cold n-propanol. After the solid has dried 44 g of the product are obtained as the hydrochloride.

Mass spectrum (ESI⁺): m/z=359 [M+H]⁺

Process Step M 300 mg palladium (10%) on charcoal are added to a mixture of 1.7 g benzyl(trans)-9-(3-benzyl-7-methoxy-4-oxo-3,4-dihydro-quinazoline-6-yloxy)-5-oxo-1,4-diaza-spiro[5.5]undecane-1-carboxylate in 30 ml acetic acid and 3 ml of water. After 22 h hydrogenation at 70° C. the mixture is filtered and the solution is evaporated to dryness, yielding 1.3 g of product.

Mass spectrum (ESI⁺): m/z=359 [M+H]⁺

Example 11

(trans)-9-(4-chloro-7-methoxy-quinazolin-6-yloxy)-1,4-diaza-spiro[5.5]undecan-5-one

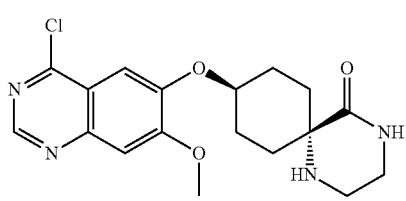

(13)

Process Step N 10 g (trans)-9-(4-hydroxy-7-methoxy-quinazolin-6-yloxy)-1,4-diaza-spiro[5.5]undecan-5-one hydrochloride and 12 g triphenylphosphine are suspended in 450 ml dioxane. Then 250 ml of solvent are distilled off and 6.45 g of N-chlorosuccinimide in 100 ml acetonitrile are added dropwise at 41° C. The reaction mixture is refluxed. After 100 min the mixture is cooled to 29° C. and 150 ml of methyltetrahydrofuran are added. The precipitate is filtered off and washed three times with 50 ml of methyltetrahydrofuran. After drying at 30° C., 12 g of a dark coloured solid are obtained, which contains the product as the hydrochloride, and which is reacted further in the next step without purification.

Mass spectrum (ESI⁺): m/z=377 [M+H]⁺

Example 12

(trans)-9-[4-(3-chloro-2-fluoro-phenylamino)-7-methoxy-quinazolin-6-yloxy]-1,4-diaza-spiro[5.5]undecan-5-one

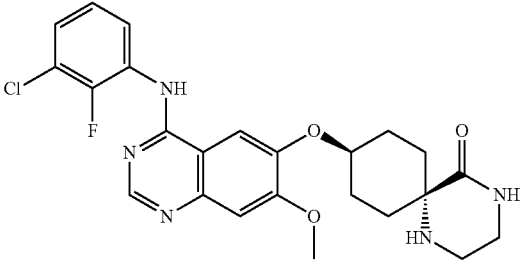

(1B)

Process Step O 12 g of the impure (trans)-9-(4-chloro-7-methoxy-quinazolin-6-yloxy)-1,4-diaza-spiro[5.5]undecan-5-one hydrochloride from the previous step are added batchwise to a solution of 3.9 g of 3-chloro-2-fluoroaniline in 60 ml of 2N hydrochloric acid at RT within 90 min. The suspension is heated to 40° C. for 60 min. Then 60 ml of toluene are added and the mixture is cooled to RT. After 50 min it is filtered and the precipitate is washed with 50 ml of toluene and 50 ml of sat. NaCl solution. After drying at 40° C., 10 g of a solid are obtained, which contains the product. The product is purified by basic chromatography on silica gel.

Mass spectrum (ESI⁺): m/z=486 [M+H]⁺

1H NMR (400 MHz, DMSO): 9.60 (1H, s); 8.37 (1H, s); 7.82 (1H, s); 7.45-7.54 (2H, m), 7.36 (1H, s); 7.28 (dt, 1H); 7.22 (1H, s); 4.63-4.67 (1H, m); 3.95 (3H, s); 3.11-3.15 (2H, m); 2.82-2.86 (2H, m); 2.30 (1H, s); 2.13-2.22 (2H, m); 1.83-1.96 (4H, m); 1.44-1.51 (2H, m).

Example 13

1-benzyl 4-tert-butyl(trans)-9-(3-benzyl-7-methoxy-4-oxo-3,4-dihydro-quinazolin-6-yloxy)-5-oxo-1,4-diaza-spiro[5.5]undecane-1,4-dicarboxylate

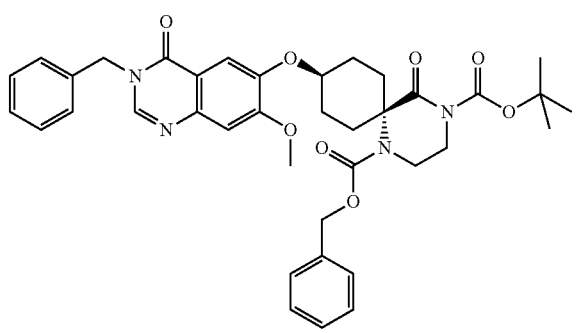

(7S)

Process Step P 1.36 ml diisopropylazo-dicarboxylate are added dropwise within 90 min to a suspension of 1.3 g of 3-benzyl-6-hydroxy-7-methoxy-3H-quinazolin-4-one, 2 g of 1-benzyl 4-tert-butyl (cis)-9-hydroxy-5-oxo-1,4-diaza-spiro[5.5]undecane-1,4-dicarboxylate and 1.8 g triphenylphosphine in 10 ml N-methyl-2-pyrrolidone. The mixture is stirred for 4 h. The mixture which contains the product is used directly in the next step.

Mass spectrum (ESI+): m/z=683 [M+H]+

Example 14

Benzyl(trans)-9-(3-benzyl-7-methoxy-4-oxo-3,4-dihydro-quinazolin-6-yloxy)-5-oxo-1,4-diaza-spiro[5.5]undecane-1-carboxylate

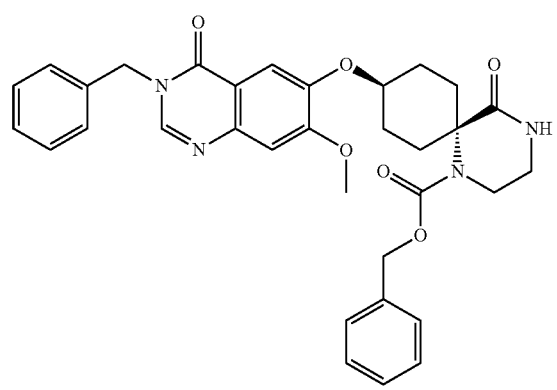

(8S)

Process Step Q 2.5 ml of 4 M HCl in dioxane are added to the mixture from the previous step which contains the 1-benzyl 4-tert-butyl (trans)-9-(3-benzyl-7-methoxy-4-oxo-3,4-dihydro-quinazolin-6-yloxy)-5-oxo-1,4-diaza-spiro[5.5]undecane-1,4-dicarboxylate. After 19 h, 2 ml of 4 M HCl in dioxane are added and the mixture is heated to 40° C. After 3 h the temperature is increased to 60° C., the mixture is diluted with 60 ml dioxane and 10 ml of 4 M HCl in dioxane are added. After 16 h the mixture is evaporated down in vacuo and the residue is taken up in 50 ml dichloromethane. After three washes, with 50 ml of water in each case, the organic phase is evaporated down. The residue is purified by chromatography on silica gel. The corresponding fractions are evaporated down and the residue is decocted with 150 ml ethyl acetate. After isolation and drying of the precipitate, 2.1 g of product are obtained.

Mass spectrum (ESI+): m/z=583 [M+H]+

Example 15

Benzyl(cis)-9-(3-benzyl-7-methoxy-4-oxo-3,4-dihydro-quinazolin-6-yloxy)-5-oxo-1,4-diaza-spiro[5.5]undecane-1-carboxylate

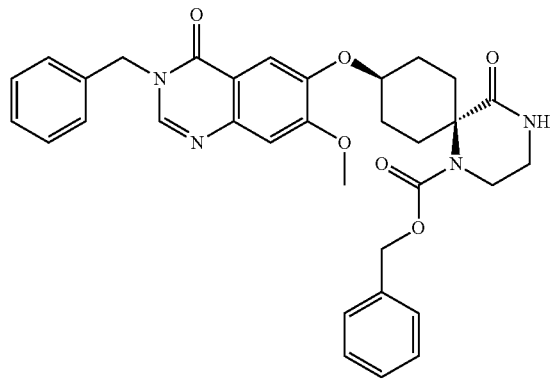

(21S)

Process Step R 2.1 ml of diisopropyl azo-dicarboxylate are added dropwise, with cooling, to a mixture of 2 g of 3-benzyl-6-hydroxy-7-methoxy-3H-quinazolin-4-one, 2.37 g of benzyl(trans)-9-hydroxy-5-oxo-1,4-diaza-spiro[5.5]undecane-1-carboxylate and 2.79 g of triphenylphosphine in 20 ml of N-methyl-2-pyrrolidone. After 20 min, 20 ml of N-methyl-2-pyrrolidone are added and the mixture is stirred for 4 h. The precipitate is suction filtered at 0° C. and washed with 50 ml of methyl-tert-butylether. After drying, 3.3 g of product are obtained which still contains N-methyl-2-pyrrolidone.

Mass spectrum (ESI+): m/z=583 [M+H]+

Example 16

(cis)-9-(4-hydroxy-7-methoxy-quinazolin-6-yloxy)-1,4-diaza-spiro[5.5]undecan-5-one (22)

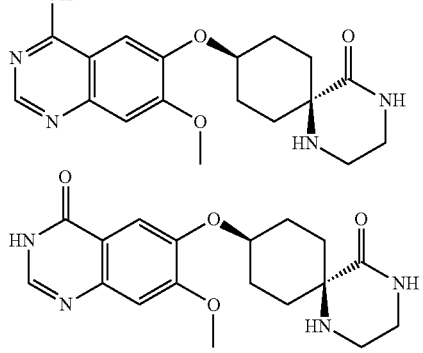

Process Step S 300 mg of palladium (10%) on charcoal are added to a mixture of 1.7 g benzyl(cis)-9-(3-benzyl-7-methoxy-4-oxo-3,4-dihydro-quinazolin-6-yloxy)-5-oxo-1,4-diaza-spiro[5.5]undecane-1-carboxylate in 30 ml of ethanol and 10 ml of 1 M hydrochloric acid. After 25 h hydrogenation at 80° C. the mixture is filtered and the solution is evaporated to dryness, thus yielding 1.4 g of crude product. The crude product is decocted with 100 ml of ethanol and after filtration the filtrate is evaporated down. The residue is suspended in 50 ml acetonitrile and after the addition of 1 g potassium carbonate it is stirred for 23 h. The mixture is evaporated down and after the addition of 20 ml of dichloromethane and 4 ml of methanol it is purified by chromatography on silica gel. 500 mg of product are obtained.

Mass spectrum (ESI⁺): m/z=359 [M+H]⁺

Example 17

(cis)-9-[4-(3-chloro-2-fluoro-phenylamino)-7-methoxy-quinazolin-6-yloxy]-1,4-diaza-spiro[5.5]undecan-5-one

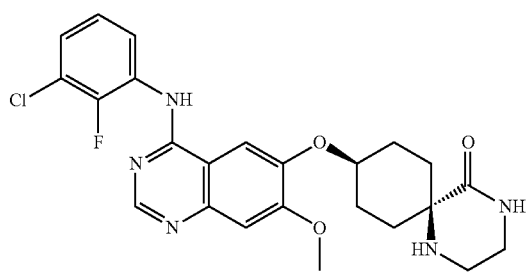

(1A)

Process Step T 0.13 ml phosphorus oxytrichloride are added to a mixture of 100 mg of 7-methoxy-6-(5-oxo-1,4-diaza-spiro[5.5]undec-9-yloxy)-3H-quinazolin-4-one and 0.23 ml of triethylamine in 5 ml of acetonitrile. After 1 h, 0.04 ml of 3-chloro-2-fluoroaniline are added. After 18 h, 1 ml of water is added and the mixture is evaporated down to a volume of 2 ml. After purification by preparative HPLC, 95 mg of product are obtained.

Mass spectrum (ESI⁺): m/z=486 [M+H]⁺

1H NMR (400 MHz, DMSO): 9.58 (1H, s); 8.36 (1H, s); 7.81 (1H, s); 7.54 (1H, t); 7.49 (1H, t); 7.42 (1H, s); 7.29 (1H, t), 7.20 (1H, s); 4.49-4.58 (1H, m); 3.93 (3H, s); 3.11-3.15 (2H, m); 2.80-2.85 (2H, m); 2.38 (1H, s); 1.88-2.02 (4H, m); 1.69-1.81 (4H, m).

Example 18

(trans)-9-hydroxy-1,4-diaza-spiro[5.5]undecan-5-one hydrochloride (cis)-9-hydroxy-1,4-diaza-spiro[5.5]undecan-5-one hydrochloride

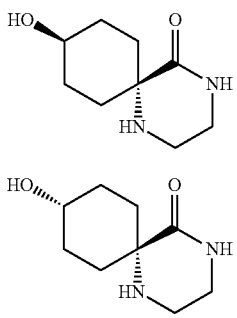

(17a)

(17b)

Process Step U 50 mg of platinum dioxide are added to a mixture of 500 mg of 1,4-diaza-spiro[5.5]undecane-5,9-dione hydrochloride in 5 ml of water. After 3 h hydrogenation the mixture is filtered and the solution is evaporated down to dryness. It is evaporated twice with 50 ml of n-propanol and 500 mg of a trans/cis mixture of 9-hydroxy-1,4-diaza-spiro[5.5]undecan-5-one hydrochloride are left.

Mass spectrum (ESI⁺): m/z=185 [M+H]⁺

Example 19

Benzyl 5,9-dioxo-1,4-diaza-spiro[5.5]undecane-1-carboxylate

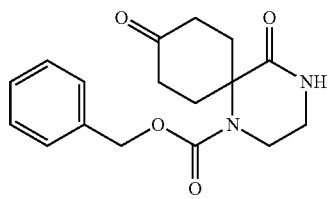

(19S)

Process Step V 14.4 ml benzyl chloroformate are added, with cooling, to a mixture of 20 g of 1,4-diaza-spiro[5.5]undecane-5,9-dione hydrochloride in 100 ml of tetrahydrofuran and 82 ml of 50% potassium carbonate solution. After 2.5 h, 250 ml of water are added and the precipitate is filtered off. After washing with 200 ml of water and 200 ml methyl-tert-butylether and drying, 24.3 g of product is obtained.

Mass spectrum (ESI⁺): m/z=317 [M+H]⁺

Example 20

Benzyl(trans)-9-hydroxy-5-oxo-1,4-diaza-spiro[5.5]undecane-1-carboxylate

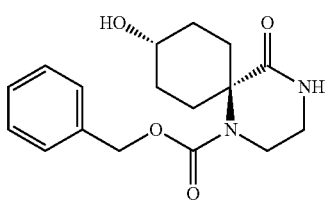

(18S)

Process Step W 50 mg platinum dioxide are added to a mixture of 5 g of 1,4-diaza-spiro[5.5]undecane-5,9-dione hydrochloride in 20 ml of water. After 22 h hydrogenation 25 mg of platinum dioxide are added. After 26 h hydrogenation the mixture is filtered and the filtrate is combined with 35 g of potassium carbonate and 25 ml of tetrahydrofuran. 3.43 ml of benzyl chloroformate are added and the mixture is stirred for 6 d. 25 g of potassium carbonate are added and the mixture is stirred for 4 d. 3.5 ml of benzyl chloroformate are added. After 20 h, 200 ml of water are added and after another 1 h stirring the precipitate is suction filtered and washed with 100 ml of methyl-tert-butylether. 3.4 g of solid are obtained, which consists primarily of the product.

Mass spectrum (ESI⁺): m/z=319 [M+H]⁺

Process Step X 7.2 g sodium borohydride are added to 20 g of benzyl 5,9-dioxo-1,4-diaza-spiro[5.5]undecane-1-carboxylate in 100 ml of tetrahydrofuran, 100 ml of ethanol, 80 ml of water and 20 ml of 0.1 N sodium hydroxide solution. After 16.5 h stirring at RT and 1 h at 60° C., 80 ml of 2M hydrochloric acid and 200 ml of water are added dropwise while cooling with ice. After 2 h the precipitate is suction filtered and washed with 200 ml of water. After the precipitate has been dried and purified by chromatography on silica gel, 8 g of product are isolated.

Mass spectrum (ESI$^+$): m/z=319 [M+H]$^+$

Example 21

1-benzyl 4-tert-butyl(trans)-9-hydroxy-5-oxo-1,4-diaza-spiro[5.5]undecane-1,4-dicarboxylate

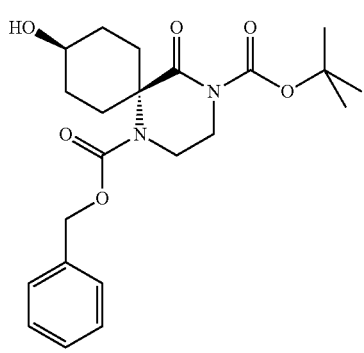

(20S)

Process Step Y

A mixture of 200 mg of benzyl(trans)-9-hydroxy-5-oxo-1,4-diaza-spiro[5.5]undecane-1-carboxylate, 87 mg of potassium carbonate, 274 mg of di-tert-butyldicarbonate and 76 mg of 4-(dimethylamino)-pyridine in 5 ml of acetonitrile are stirred for 2 h at RT. The mixture is purified by preparative HPLC and 100 mg of product are obtained.

Mass spectrum (ESI$^+$): m/z=419 [M+H]$^+$

Example 22

Benzyl(cis)-9-hydroxy-5-oxo-1,4-diaza-spiro[5.5]undecane-1-carboxylate

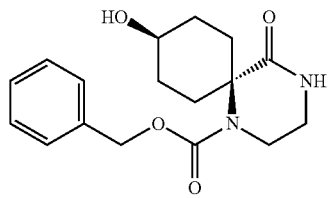

(16S)

Process Step Z 14.3 g of sodium borohydride are added batchwise at RT to a solution of 75 g of, 4-diaza-spiro[5.5]undecane-5,9-dione hydrochloride in 350 ml of 1M sodium hydroxide solution. After 35 min, 60 ml conc. hydrochloric acid are added dropwise within 30 min. with cooling. 390 g of potassium carbonate are added. After the addition of 300 ml of tetrahydrofuran and 67 ml of benzyl chloroformate the mixture is heated to 48° C. for 1.5 h. 900 ml of methyl-tert-butylether are added and after cooling to 22° C., 1.6 l of water are added. After 1 h stirring the suspension is suction filtered and the filter cake is washed with 500 ml of water and 1 l methyl-tert-butylether. After the filter cake has dried, 77 g product are obtained, consisting predominantly of the cis isomer.

Mass spectrum (ESI$^+$): m/z=319 [M+H]$^+$

Example 23

Methyl(cis)-1-(2-tert-butoxycarbonylamino-ethylamino)-4-hydroxy-cyclohexanecarboxylate

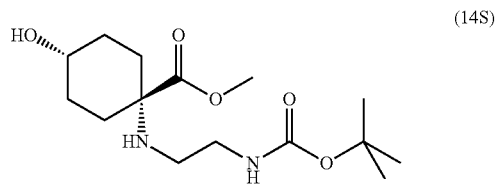 [SMILES: COC(=O)[C@]1(NCCNC(=O)OC(C)(C)C)CC[C@@H](O)CC1]

(14S)

Process Step ZZ 16.7 mg sodium borohydride are added to a solution of 500 mg of tert-butyl 5,9-dioxo-1,4-diaza-spiro[5.5]undecane-4-carboxylate in 5 ml of methanol. After 4 h the mixture is evaporated down and evaporated with tetrahydrofuran. The residue contains the product.

Mass spectrum (ESI$^+$): m/z=317 [M+H]$^+$

Example 24 tert-butyl(cis)-[2-(4-hydroxy-1-hydroxymethyl-cyclohexylamino)-ethyl]-carbamate

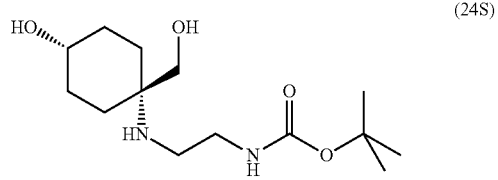 [SMILES: CC(C)(C)OC(=O)NCCN[C@]1(CO)CC[C@H](O)CC1]

(24S)

Process Step ZZZ 161 mg sodium borohydride are added to a mixture of 1 g of tert-butyl 5,9-dioxo-1,4-diaza-spiro[5.5]undecane-4-carboxylate in 10 ml of 1 M potassium carbonate solution with cooling. After 14.5 h at 50° C., 10 ml of ethyl acetate are added and after phase separation the organic phase is evaporated down. After chromatographic purification of the residue on silica gel, 580 mg of a mixture containing the product are isolated.

Mass spectrum (ESI$^+$): m/z=289 [M+H]$^+$

The invention claimed is:
1. A compound of formula (13)
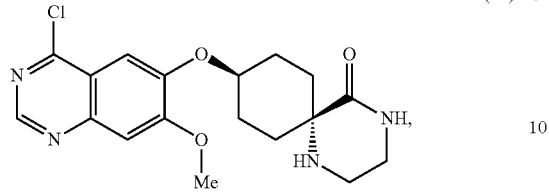
as well as the physiologically acceptable salts thereof with inorganic or organic acids and bases.
* * * * *